United States Patent [19]

Repke

[11] 4,336,803
[45] Jun. 29, 1982

[54] SHAPED ABSORBENT PAD FOR DISPOSABLE DIAPERS

[75] Inventor: Virginia L. Repke, Oak Forest, Ill.

[73] Assignee: Johnson & Johnson Baby Products Company, New Brunswick, N.J.

[21] Appl. No.: 104,518

[22] Filed: Dec. 17, 1979

Related U.S. Application Data

[63] Continuation-in-part of Ser. No. 865,464, Dec. 29, 1977, abandoned.

[51] Int. Cl.³ .............................................. A41B 13/02
[52] U.S. Cl. .................................................. 128/287
[58] Field of Search ................................. 128/284, 287

[56] References Cited

U.S. PATENT DOCUMENTS

| 2,627,858 | 2/1953 | Miller | 128/287 |
| 3,386,442 | 6/1968 | Sabee | 128/287 |
| 3,402,715 | 9/1968 | Liloia et al. | 128/287 |
| 3,766,922 | 10/1973 | Krusko | 128/284 |
| 3,837,343 | 9/1974 | Mesek | 128/284 |
| 3,860,003 | 1/1975 | Buell | 128/287 |
| 4,050,462 | 9/1977 | Woon et al. | 128/287 |
| 4,205,679 | 6/1980 | Repke et al. | 128/287 |

FOREIGN PATENT DOCUMENTS 1164469 9/1969 United Kingdom ............... 128/287

Primary Examiner—C. Fred Rosenbaum
Attorney, Agent, or Firm—Martha A. Michaels

[57] ABSTRACT

An improved disposable diaper containing a shaped absorbent pad. The pad has an indentation disposed along each long side nearer one end of the pad than the other. The front half of each indentation is arcuate and the back half of each indentation is triangular in shape. The sides of the pad immediately adjacent the indentations in the central portion of the pad are parallel to the center longitudinal line.

8 Claims, 9 Drawing Figures

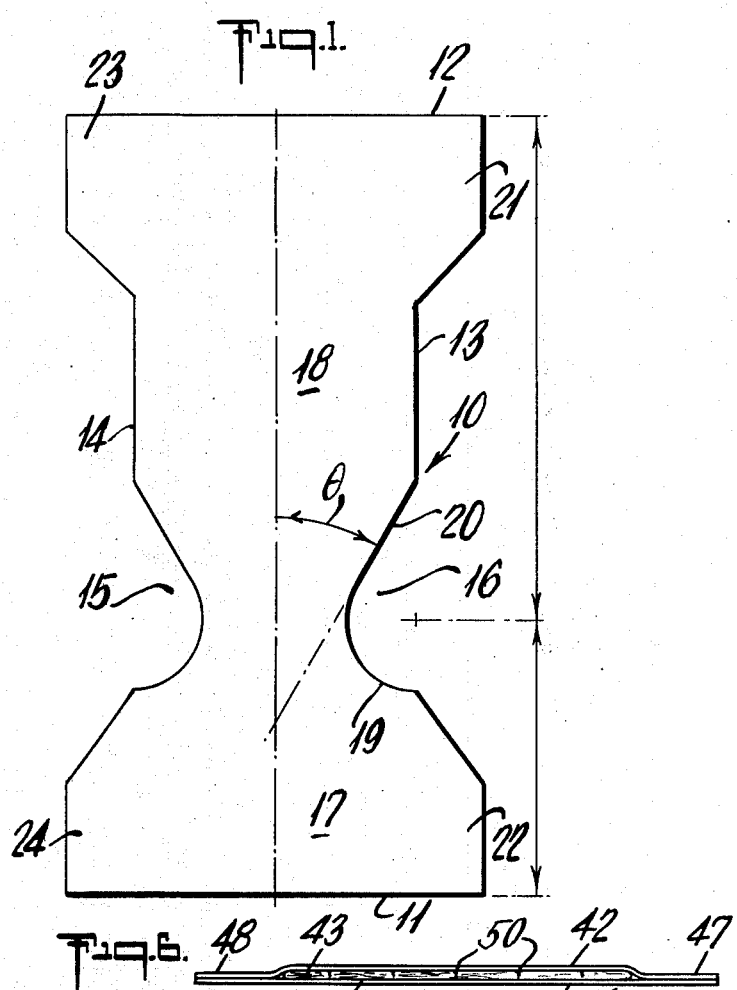
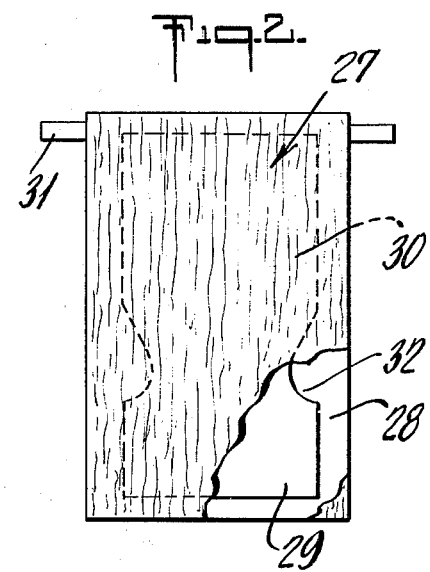
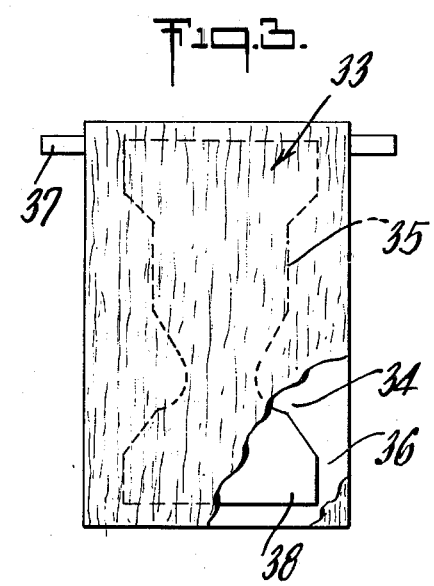
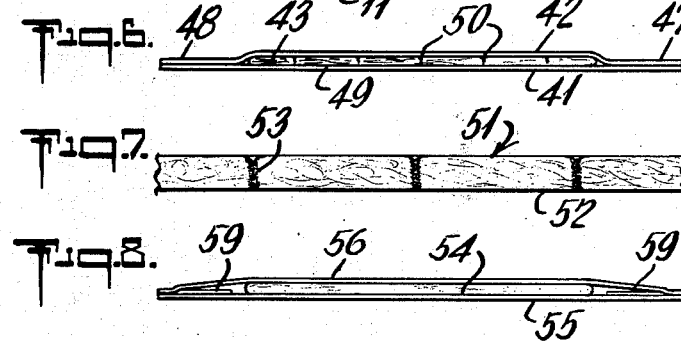
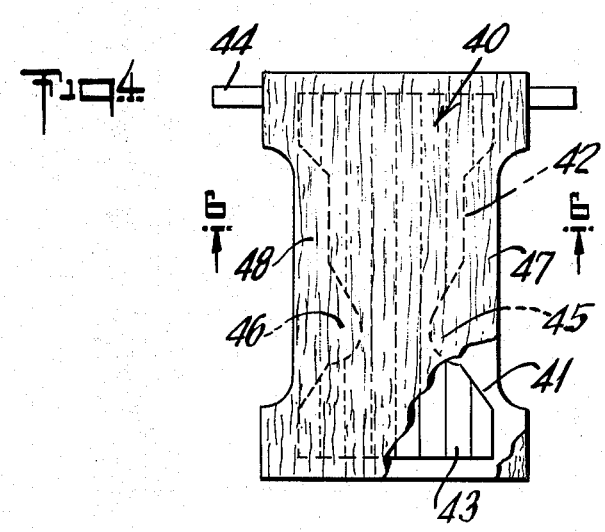
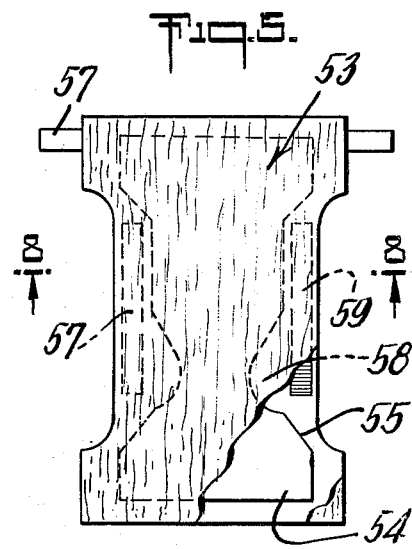

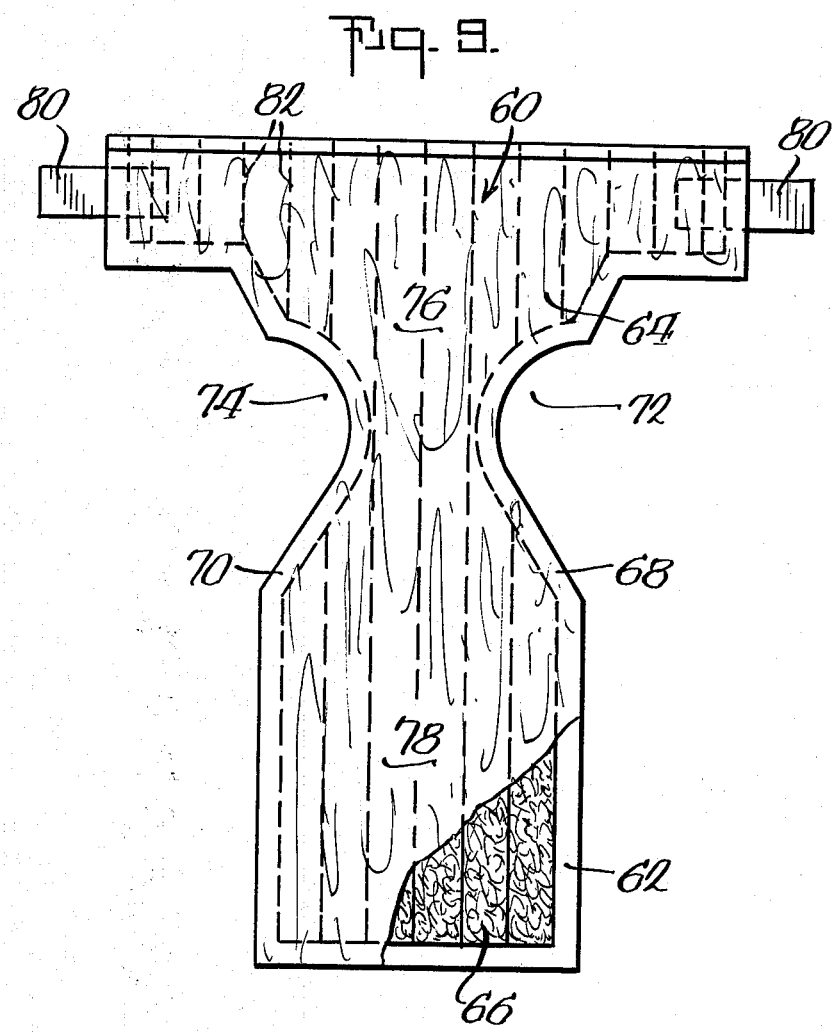

SHAPED ABSORBENT PAD FOR DISPOSABLE DIAPERS

This application is a continuation-in-part of copending application, U.S. Ser. No. 865,464, filed Dec. 29, 1977 and now abandoned.

BACKGROUND OF THE INVENTION

The present invention relates to shaped absorbent pads for use in disposable diapers.

Disposable diapers have and are continuing to gain wide acceptance as a substitute for previously used cloth diapers and as an adjunct to such cloth diapers. Most disposable diapers have been rectangular in shape and folded in a manner to aid in their application about the buttocks of the baby. In some instances, the diapers have been folded in geometric configurations to aid in their application to the baby. Also, some diapers contain hourglass shaped absorbent panels; that is, absorbent panels which are narrow in the center portion and wide at the front and rear end portions.

It has been known for some time now that if the bulk of the diaper could be reduced in the area between the legs of the wearer the fit of the diaper would be improved. However, reducing the bulk in the area between the legs means reducing the amount of absorbent material used in that area, an area where absorbency is very important.

What I have discovered is a new and improved shaped absorbent pad for use in disposable diapers. My new and improved shaped pad reduces the bulk between the baby's legs while maintaining excellent absorptive efficiency of the pad both in the front portion and the rear portion of the pad. Furthermore, my improved pad provides an excellent fit about the baby's legs themselves to produce an aesthetically appealing diaper and a more stable diaper during use.

SUMMARY OF THE PRESENT INVENTION

The improved pad of the present invention is substantially rectangular in shape or a T-shape. The pad has a pair of short parallel ends and a pair of long parallel sides perpendicular to said ends. Disposed in opposed relationship on each longitudinal side is an indentation. The deepest point of each indentation is positioned at approximately one-third the length of the rectangular panel to divide the pad into a short portion to be positioned in front of the baby and a longer rear portion to extend between the baby's legs and behind the buttocks. The front edge of each indentation is arcuate and the front half of each indentation has substantially the shape of a minor portion of a circle, the arc of which ranges from about 90° to about 120°. The rear edge of each indentation has a uniformly straight slope from the deepest part of the indentation to the longitudinal side of the pad at an angle of from about 30 to 45 degrees to the center of the sides of the pad. The rear half of each indentation has a substantially triangular shape.

By virtue of the above-described shape, maximum absorptive capacity of the pad is retained in the crotch region; while at the same time improved fit around the legs of the baby is provided.

In a preferred embodiment of the pad of the present invention, the four corners have extended portions to provide the pad with extra absorbent capacity. In another embodiment of my improved pad, the cross-sectional shape of the pad is contoured with the center portion of the pad being thicker than the edge portions of the pad to provide extra absorbency in the central area.

The improved pad of the present invention is usually used between a pervious or permeable facing layer which is soft and is disposed against the baby's skin and may be of such material as to maintain the baby's skin relatively dry while the diaper is being worn and a backing layer on the opposite side of the pad from the facing layer. The backing layer is generally an impervious film material to prevent strike-through of liquid. In some embodiments, my improved pad may contain a densified paperlike skin area and one or more densified compacted geometrical areas to improve the wicking, capillarity and distribution of liquid through the absorbent pad and improve its efficiency.

BRIEF DESCRIPTION OF THE DRAWINGS

The invention will be more fully described in conjunction with the accompanying drawings wherein:

FIG. 1 is a plan view of the improved pad of the present invention;

FIG. 2 is a plan view of a disposable diaper incorporating the improved pad of the present invention with a portion broken away to show the various layers;

FIG. 3 is a plan view of another embodiment of a disposable diaper incorporating the improved pad of the present invention;

FIG. 4 is a plan view of another embodiment of a disposable diaper incorporating the improved pad of the present invention with a portion broken away to show the various layers;

FIG. 5 is another embodiment of a disposable diaper incorporating the pad of the present invention with portions broken away to show the various layers;

FIG. 6 is a cross-sectional view along line 6—6 of FIG. 4;

FIG. 7 is an enlarged cross-sectional view of a portion of an embodiment of the improved pad of the present invention;

FIG. 8 is another cross-sectional view of another embodiment of the pad of the present invention;

FIG. 9 is a plan view of another embodiment of a disposable diaper incorporating the improved pad of the present invention with a portion broken away to show the various layers.

DETAILED DESCRIPTION OF THE DRAWINGS

As shown in FIG. 1, the absorbent pad of the present invention has a substantially rectangular shape. The pad has parallel opposite end margins 11 and 12 and parallel opposite longitudinal side margins 13 and 14. Along the longitudinal margins there are disposed indentations 15 and 16. The deepest part of the indentations is approximately one-third along the length of the pad to form a smaller front portion 17 and a larger rear portion 18. The front edge 19 of each indentation is arcuate and the front half of the indentation has the shape of a 120° segment of a circle. In use, the front edge contacts the inner and front portion of the baby's leg or thigh to provide a good fit in that area. The rear edge 20 of the indentation is generally uniformly sloped from the deepest part of the indentation to the longitudinal edge portion. In use, this rear edge fits about the rear of the baby's leg or thigh to provide a good fit in that area. The sloped rear edge makes an angle of about 30 to 45 degrees to the center line of the diaper. The side margins adjacent the indentations in the central portion of the pad are parallel with one another. This configuration provides the improved fit with a minimum loss of absorptive capacity. As shown in this FIG. 1, the four corners 21, 22, 23, and 24 contain extended longitudinal side portions which fit about the waist area of the wearer and provide increased absorbent material and capacity in the pad. The size and shape of the corners may vary greatly depending on the type and size of the diaper being produced.

The indentations, depending on whether the diaper is a newborn size, toddler size, or other size, will vary from about an inch to two inches in depth and preferably from about 1¼ to 1¾ inches in depth. The front edge or circle segment is on a radius similar to the depth or equal to the depth dimension. The distance the deepest part of the indentation may be from the front end margin of the absorbent pad may vary from about four to six inches and from about 30% to 40% of the total length of the pad and preferably from about 30% to 35% of the total length of the pad to provide the desired fit and aesthetically shaped pad. In some embodiments of the indentation, the portion of the front edge which meets the longitudinal side of the pad may be a straight portion; i.e., perpendicular to the side, depending on the size of the diaper being produced. The gently sloped rear edge, where it starts from the deepest part of the indentation, may also be gently rounded before it straightens out to its desired slope, again depending on the size of the diaper being produced. The indentation as described provides a close, neat fit around the wide variety of leg sizes.

The narrowed crotch area; i.e., the dimension of the pad between indentations, may also be varied according to diaper size. This dimension may be as small as 3 to 3½ inches for a newborn size diaper or as large as 4½ inches or more for toddler or other large size diapers. I have found a narrowed crotch area dimension of 3½ to 4 inches to be satisfactory for most size diapers.

In FIG. 2, there is shown a diaper 27 comprising an impervious backing sheet 28, shaped absorbent pad 29, and a pervious or permeable facing sheet 30. At one end of the diaper along both longitudinal side margins are a pair of adhesive tape tabs 31 for affixing the diaper about the infant. The pad 29 has two parallel end margins and two parallel longitudinal side margins. Disposed along each longitudinal side portion is an indentation 32 with the indentations opposite each other. The indentations have a 120° circle segment front portion and a uniformly sloped back portion and are positioned approximately one-third of the distance along the length of the pad.

In the embodiment in FIG. 3, there is shown a diaper 33 having backing sheet 34, a pervious facing sheet 35 and a substantially rectangular absorbent pad 36. At one end of the diaper, are a pair of tape tabs 37 for affixing the diaper about the infant. The pad shown in this embodiment includes four outwardly extending corners 38. These corners provide extra absorbent material to increase the capacity of the pad.

Referring to FIG. 4, there is shown another embodiment of a disposable diaper 40 incorporating the newly shaped pad of the present invention. The diaper comprises a shaped impervious film backing member 41 and a coextensive shaped pervious facing member 42 with a shaped pad 43 of the present invention disposed therebetween. At one end of the diaper are a pair of oppositely disposed tape tabs 44 for affixing the diaper about the baby. The shaped pad has a pair of oppositely disposed shaped indentations 45 and 46 along the longitudinal side edges of the pad. As seen, the shaped indentations have a circle segment front portion and a gently sloped rear edge. The longitudinal edges 47 and 48 of the facing and backing layers are indented to provide the diaper with an overall shape.

As seen in the cross-sectional view shown in FIG. 6, the facing 42 and backing 41 layers are sealed together along their longitudinal edges 47 and 48 and the absorbent pad includes a wicking layer, or dense area 49 at the surface next to the backing layer and a plurality of densified or compacted longitudinal lines 50 to aid in the wicking and distribution of fluid being absorbed by the pad.

As may be more clearly seen in the enlarged cross-sectional view of FIG. 7, the absorbent pad 51, in many embodiments of the present invention, may have a densified surface 52 preferably the surface which is disposed adjacent the impervious backing member. This densified paper-like surface may be formed by applying moisture to the pad and applying pressure as disclosed in U.S. Pat. No. 3,017,304 or U.S. Pat. No. 3,993,820. The later patent includes the addition of longitudinally densified lines 53 to provide for improved capillarity, wicking and distribution of liquids absorbed by the pad.

Referring to FIGS. 5 and 8, there is shown another embodiment of a disposable diaper 53 which incorporates the newly shaped pad 54 of the present invention. In this embodiment the backing layer 55 is shaped as described in conjunction with FIG. 4 and the coextensive facing layer 56 is similarly shaped. An end portion of the diaper contains oppositely disposed adhesive tabs 57 for affixing the diaper to the baby. The shaped pad of the present invention is disposed between the backing and facing layers and contain the indentations 58 disposed approximately one-third along the length of the pad. Along the longitudinal side edges of the pad are rubber strips 59 which are inserted in the diaper in their extended or stretched state, sealed to the backing and/or facing layer and allowed to relax to provide elastic sides in the diaper to provide a tight fit about the baby's legs.

Referring to FIG. 9 there is shown another embodiment of a disposable diaper 60 incorporating the newly shaped pad of the present invention. The diaper comprises a shaped impervious film backing member 62 and a coextensive shaped pervious facing member 64 with a shaped pad 66 of the present invention disposed therebetween. Along the longitudinal margins 68 and 70 there are disposed indentations 72 and 74. The deepest part of the indentations is approximately one-third along the length of the pad to form a shorter front portion 76 and a longer rear portion 78. At the front end of the diaper are a pair of oppositely disposed tape tabs 80 for affixing the diaper about the baby. The shaped indentations 72 and 74 have a circle segment front portion and a triangular shaped rear portion. The overall shape of the diaper 60 is similar to a "T" shape.

The absorbent pads of the present invention are preferably formed of loosely compacted, short cellulose fibers, such as wood pulp fibers, or cotton linters, or mixtures thereof, which are primarily held together by interfiber bonds requiring no added adhesive, as is known in the art.

The term "short fibers" as used herein, refers to fibers less than about ¼ inch in length, in contrast to "long fibers" or "textile length fibers" which are longer than about ¼ inch in length, and generally are between ½ inch and 2½ inches in length.

The backing layers used in making the disposable diapers of the present invention may be any of the thermoplastic films such as polyethylene, polypropylene and the like and may contain perforations or breathing areas as desired if these areas are placed in such a manner as not to allow liquid to pass through.

The facing layers may be any of the facing layers presently used on disposable diapers including the facing layers described and disclosed in conjunction with Mesek, et al. U.S. Pat. Nos. 3,777,758 and 3,768,480 or other non-woven fabrics. Other facing layers that may be also used in the diapers of the present invention are the polyester fabrics or the perforated film materials.

The foregoing description and the drawings are intended as illustrative and are not to be taken as limiting. Still other variations are possible without departure from the spirit and scope of this invention.

I claim:

1. A shaped disposable diaper comprising; an impervious backing layer and a pervious facing layer, said layers being coextensive, and an absorbent pad disposed between said layers and spaced inwardly from the end margins and side margins of said facing and backing layers, said facing and backing layers having their greatest width at said end margins and a narrower width between said end margins, said pad having its widest portions adjacent the end margins and being narrower in the center portion of the pad, said pad having an indentation in each longitudinal edge adjacent said side margins, said indentations being disposed symmetrically opposite each other and being positioned approximately one-third the distance from one end of the pad to provide a short area between the one end of the pad and a first portion of the indentation, and a long area between the opposite end of the pad and a second portion of the indentation, the first portion of the indentation having substantially the shape of a minor portion of a circle having an arc from about 90° to about 120°, providing the deepest part of the indentation, a second portion of each indentation being formed by a line of uniformly straight slope from the deepest part of the indentation to the longitudinal side of the pad at an angle from about 30° to about 45° to the sides of the pad, the second portion of each indentation having a substantially triangular shape.

2. A shaped diaper according to claim 1 wherein an elastic member is disposed in each side margin between the facing and backing layers and adjacent the pad.

3. A diaper according to claim 1 wherein the pad includes a densified, compacted layer on one of the surfaces of the pad.

4. A diaper according to claim 1 wherein the pad includes a plurality of densified and compacted areas disposed throughout the pad to improve absorbency and stability of the pad.

5. A diaper according to claim 1 wherein said arcuate front edge is approximately 120°.

6. A substantially rectangular shaped absorbent pad having one indentation in each long side, each indentation being disposed symmetrically opposite the other, and being positioned approximately one-third the distance from one end of the pad to provide a short area between the one end of the pad and a first portion of the indentation, and a long area between the opposite end of the pad and a second portion of the indentation, the first portion of the indentation having substantially the shape of a minor portion of a circle, the arc of which ranges from about 90° to about 120°, providing the deepest part of the indentation, a second portion of each indentation being formed by a line of uniformly straight slope from the deepest part of the indentation to the longitudinal side of the pad at an angle from about 30° to about 45° to the sides of the pad, the second portion of each indentation having a substantially triangular shape.

7. An absorbent pad according to claim 6 wherein the four corners of the pad extend outwardly beyond the long sides of the pad.

8. An absorbent pad according to claim 6 wherein two corners at one end of the pad extend outwardly beyond the long sides of the pad.

* * * * *